(12) United States Patent
Wallach et al.

(10) Patent No.: US 8,318,660 B2
(45) Date of Patent: Nov. 27, 2012

(54) METHOD OF TREATING A DISEASE BY ADMINISTERING CASPASE-8

(75) Inventors: David Wallach, Rehovot (IL); Elena Appel, Rishon Le Zion (IL); Andrei Kovalenko, Rehovot (IL); Rajput Akhill, New Delhi (IN)

(73) Assignee: Yeda Research and Development Co. Ltd., Rehovot, IL (US)

( * ) Notice: Subject to any disclaimer, the term of this patent is extended or adjusted under 35 U.S.C. 154(b) by 1069 days.

(21) Appl. No.: 12/282,747

(22) PCT Filed: Mar. 5, 2007

(86) PCT No.: PCT/IL2007/000278
§ 371 (c)(1),
(2), (4) Date: Sep. 12, 2008

(87) PCT Pub. No.: WO2007/105199
PCT Pub. Date: Sep. 20, 2007

(65) Prior Publication Data
US 2009/0104175 A1 Apr. 23, 2009

(30) Foreign Application Priority Data
Mar. 12, 2006 (IL) .......................................... 174253

(51) Int. Cl.
*A61K 38/16* (2006.01)
*A61P 15/00* (2006.01)
*C07K 14/435* (2006.01)

(52) U.S. Cl. .......... 514/1.1; 514/1.4; 514/18.9; 530/350

(58) Field of Classification Search ........................ None
See application file for complete search history.

(56) References Cited

U.S. PATENT DOCUMENTS
5,786,173 A * 7/1998 Alnemri et al. ............... 435/69.1
5,837,837 A * 11/1998 Hunter et al. ................. 536/23.1

FOREIGN PATENT DOCUMENTS
EP          1283052 A1 *  8/2001
EP          1283052 A1 *  2/2003
WO   WO-2007046087 A2 *  4/2007

OTHER PUBLICATIONS

Skolnick et al. From genes to protein structure and function: novel applications of computational approaches in the genomic era. Trends in Biotech 18(1): 34-39, 2000.*
Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4): 132-133, 1999.*
Bork et al. Go hunting in sequence databases but watch out for the traps. Trends in Genetics. 12(10): 425-427, 1996.*
Wells. J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
Hotchkiss et al. Cell Death. N Engl J Med 361: 1570-1583, 2009.*
Pacher et al. Nitric Oxide and Peroxynotrite in health and disease. Physiol Rev 87: 315-424, 2007.*
Elmore, S. Apoptosis: A review of programmed cell death. Toxicologic Pathol 35: 495-516, 2007.*
Broker et al. Cell death independent of caspases: a review. Clin Cancer Res 11: 3155-3162, 2005.*
Rieckher et al. Acute Neuronal Injury: The Role of Excitotoxic Programmed Cell Death Mechanisms. (2010) Springer Science+Business Media, pp. 9-33.*
Soung et al. Cancer Res 65(3): 815-821, 2005.*
Soung et al. Oncogene 224: 141-147, 2005.*
Lee et al. Gastroenterol 125: 708-715, 2003.*
Halliday et al. Clin Exp Pharmacol Physiol 27: 1-8, 2000.*
Steece-Collier et al. Etiology of Parkinson's disease: genetics and environment revisited. Proc Natl Acad Sci USA 99(22): 13972-13974, 2002.*
Gokhale et al. A study of serum nitric oxide levels in psoriasis. Indian J Dermatol Venereol Leprol 71(3): 175-178, 2005.*
Januchowski, R. Evaluation of topical vitamin B12 for the treatment of childhood eczema. J Alt Complement Med 15(4): 387-389, 2009.*
Taniuchi et al. Increased serum nitrate levels in infants with atopic dermatitis. Allergy 56: 693-695, 2001.*
Sahin et al. The role of nitric oxide in allergic contact dermatitis. Arch Dermatol Res 293: 214-217, 2001.*
Trautmann et al. Role of apoptosis in atopic dermatitis. Int Arch Allergy Immunol 124: 230-232, 2001.*
Martin-Sanz et al. Nitric oxide in liver inflammation and regeneration. Metab Brain Disease 17(4): 324-334, 2002.*
Chen et al. Role of nitric oxide in liver injury. Curr Molec Med 3: 519-526, 2003.*
Kang, Tae-Bong et al., "Caspase-8 Serves Both Apoptotic and Nonapoptotic Roles." J Immunol 173:2976-2984, 2004.
Newton, Kim and Strasser, Andreas, "Caspases signal not only apoptosis but also antigen-induced activation in cells of the immune system." Genes & Development 17:819-825, 2003.
Wesche-Soldato, Doreen E. et al., "In vivo delivery of caspase-8 or Fas siRNA improves the survival of septic mice." Blood 106(7):2295-2301, 2005.
Scharner, Dörte et al., "A novel apoptosis-unrelated role of caspase-8 in endothelial progenitor cell-mediated neovascularization." Circulation 114(18):182 Suppl. S., Abstract Only, from 79th Annual Scientific Session of the American-Heart Association; Chicago, Nov. 2006.
Helfer, B. et al., "Caspase-8 Promotes Cell Motility and Calpain Activity under Nonapoptotic Conditions." Cancer Res 66(8):4273-4278, 2006.

(Continued)

*Primary Examiner* — Bridget E Bunner
(74) *Attorney, Agent, or Firm* — Nixon Peabody LLP; David S. Resnick; Leena H. Karttunen Contarino

(57) ABSTRACT

The invention relates to caspases and to extracellular use of caspases for regulating cell functions.

4 Claims, 12 Drawing Sheets

OTHER PUBLICATIONS

Castro, A. et al., "Administration to mouse of endotoxin from gram-negative bacteria leads to activation and apoptosis of T lymphocytes." Eur. J. Immunol. 28:488-495, 1998.

Ballester, I. et al., "Monochloramine induces acute and protracted colitis in the rat: Response to pharmacological treatment." Life Sciences 76:2965-2980, 2005.

Chen, T. et al., "Role of Nitric Oxide in Liver Injury." Current Molecular Medicine 3:519-526, 2003.

Ebadi, M. and S.K. Sharma, "Peroxynitrite and Mitochondrial Dysfunction in the Pathogenesis of Parkinson's Disease." Antioxidants & Redox Signaling 5(3):319-335, 2003.

Childress, B.B. and J.K. Stechmiller, "Role of Nitric Oxide in Wound Healing." Biol Res Nurs 4(1):5-15, 2002.

Nathan, C.F. and J.B. Hibbs Jr., "Role of nitric oxide synthesis in macrophage antimicrobial activity." Current Opinion in Immunology 3:65-70, 1991.

Hentze, H. et al., "In Vivo and in Vitro Evidence for Extracellular Caspase Activity Released from Apoptotic Cells." Biochemical and Biophysical Research Communications 283:1111-1117, 2001.

Matsushita, K. et al., "Nitric Oxide Regulates Exocytosis by S-Nitrosylation of N-ethylmaleimide-Sensitive Factor." Cell 115:139-150, 2003.

Garthwaite, J., "Glutamate, nitric oxide and cell-cell signalling in the nervous system." TINS 14(2):60-67, 1991.

Palmer, R.M.J. et al., "Nitric oxide release accounts for the biological activity of endothelium-derived relaxing factor." Nature 327:524-526, 1987.

Härter, L. et al., "Caspase-3 activity is present in cerebrospinal fluid from patients with traumatic brain injury." Journal of Neuroimmunology 121:76-78, 2001.

Fleming, S.D. and P.A. Campbell, "Macrophages Have Cell Surface IL-10 That Regulates Macrophage Bactericidal Activity." J Immunol 156:1143-1150, 1996.

Neufeld, A.H., "Pharmacologic neuroprotection with an inhibitor of nitric oxide synthase for the treatment of glaucoma." Brain Research Bulletin 62:455-459, 2004.

Shavali, S. et al., "Reactive Macrophages Increase Oxidative Stress and Alpha-Synuclein Nitration During Death of Dopaminergic Neuronal Cells in Co-Culture: Relevance to Parkinson's Disease." Neurochemical Research 31 (1):85-94, 2006.

Salerno, L. et al., "Progress in the Development of Selective Nitric Oxide Synthase (NOS) Inhibitors." Current Pharmaceutical Design 8:177-200, 2002.

Rekka, E.A. and M.C. Chrysselis, "Nitric Oxide in Atherosclerosis." Mini Reviews in Medicinal Chemistry 2:585-593, 2002.

Ashina, M., "Nitric oxide synthase inhibitors for the treatment of chronic tension-type headache." Expert Opin. Pharmacother. 3(4):395-399, 2002.

Toda, N. et al., "Nitric oxide and penile erectile function." Pharmacology & Therapeutics 106:233-266, 2005.

Park, J.E. and A. Barbul, "Understanding the role of immune regulation in wound healing." The American Journal of Surgery 187(Suppl.):11S-16S, 2004.

Sanders, D.B. et al., "Modulation of the Inflammatory Response in the Cardiomyocyte and Macrophage." The Journal of American Society of Extra-Corporeal Technology 33:167-174, 2001.

Willmot, M. et al., "Nitric oxide synthase inhibitors in experimental ischemic stroke and their effects on infarct size and celebral blood flow: A systematic review." Free Radical Biology & Medicine 39:412-425, 2005.

Wesche, D.E. et al., "Leukocyte apoptosis and its significance in sepsis and shock." J. Leukoc. Biol. 78:325-337, 2005.

Mattana, J. et al., "Metal-catalyzed oxidation of extracellular matrix increases macrophage nitric oxide generation." Kidney International 54:1581-1592, 1998.

Sun, Q. et al., "Long-term Air Pollution Exposure and Acceleration of Atherosclerosis and Vascular Inflammation in an Animal Model." JAMA. 294(23):3003-3010, 2005.

Bommhardt, U. et al., "Akt Decreases Lymphocyte Apoptosis and Improves Survival in Sepsis." J. Immunol 172:7583-7591, 2004.

\* cited by examiner

METHOD OF TREATING A DISEASE BY ADMINISTERING CASPASE-8

CROSS REFERENCE TO RELATED APPLICATIONS

This application is a National Phase Entry Application under 35 U.S.C. §371 of co-pending International Application PCT/IL2007/00278, filed 5 Mar. 2007, which claims benefit of Israeli application No. 174253, filed on 12 Mar. 2006.

FIELD OF INVENTION

The invention relates to caspases and to extracellular use of caspases for regulating cell functions.

BACKGROUND OF THE INVENTION

Sepsis or septic shock refers to a serious infection, localized or systemic, that is accompanied by systemic manifestations of inflammation. Sepsis due to bacteremia is often called septicemia. The more general term, systemic inflammatory response syndrome, recognizes that several severe conditions (e.g., infections, pancreatitis, burns, trauma) can trigger an acute inflammatory reaction, the systemic manifestations of which are associated with release into the bloodstream of a large number of endogenous mediators of inflammation.

It has been reported that sepsis is associated with unregulated apoptosis of cells of the immune system, particularly of lymphocytes (reviewed by Wasche et al., 2005). The critical ill patient/animal unregulated lymphocyte apoptosis in the thymus spleen, and gut-associated lymphoid tissue (GALT) may lead to immune suppression, leaving the patient/animal vulnerable to subsequent infections or unable to fight the existing sepsis, resulting in multiple organ failure (MOF). In addition, the inability of macrophages to clear dying lymphocytes/cells appropriately may allow the cells to progress to a state of secondary necrosis, producing localized bystander injury in the tissue.

One experimental model of sepsis is mice injected with increased doses of lipopolysaccharide (LPS), a component of the wall of Gram-negative bacteria. The model yields more than 85% mortality. LPS induces substantially high levels of TNF, IL-1, IL-6, and the chemokines KC and MIP-2. It has been reported that administration of LPS from Gram-negative bacteria leads to activation and massive apoptosis of T lymphocytes (Castro et al. 1998).

Another model of sepsis is cecal ligation and puncture (CLP). Mice subjected to CLP-induced peritonitis manifest an early hyperdinamic metabolic response and as sepsis progresses, hypodynamic phase and death.

Bommhardt et al. (2004) reported results on animal model of sepsis showing that a major defect in sepsis is impairment of adaptive immune system suggesting that strategies to prevent lymphocyte apoptosis represent a potential important new therapy in sepsis. The results in the report show that mice which overexpress the constitutively active serine/threonine kinase (Akt), which is a potent regulator of cell proliferation and cell survival and prevent cell death in a variety of settings, showed less apoptosis in lymphocytes and improved survival following induction of sepsis.

Organ damage and mortality associated with sepsis in mouse models was reported to be caused, at least in part, due to induction of apoptosis trough activation of the Fas-FasL signaling pathway (referred herein as the "Fas pathway").

Recently, it was reported that antiapoptotic treatments improve septic outcome (Wasche-Soldate et al. 2005). For example, injection of mice with small interfering RNA (siRNA) targeted against caspase-8 (to reduce caspase-8 in cell), a downstream caspase in the FAS pathway, was shown to attenuate the onset of morbidity and mortality in sepsis. Silencing of caspase-8 by siRNA suppressed apoptosis in the spleen and liver and conferred a significant increase in the survival of septic mice. The types of cells that are targeted by the siRNA treatment, treatment that enables the animal to survive in this model of sepsis, were not identified.

Caspases are known as intracellular cysteine proteases having a central role in apoptosis. Caspases are synthesized as inactive pro-enzyme precursors and are activated by proteolytic processing. The proteolytic activity of the caspases is required for the execution of cell death.

The release of activated caspases from apoptotic cells was reported to occur in pathological situations that are characterized to be associated with classical apoptotic death. The reports do not provide any clue as to the functional significance of this release. Speculations raised in them as to this functional significance were only about the possibility that the extracellular caspases have by themselves some prejudicial effects. For example, significant caspase cleaving activity was found in plasma of mice with fulminant CD95-triggered hepatitis, and in cerebrospinal fluid (CSF) from traumatic brain injury (TBI) patients (Harter et al. 2001 and Hentze et al. 2001). Harter (2001) shows the presence of active caspase-3 in CSF from patients with severe head injury. The report shows that active caspase-3 is released from apoptotic cells in the injured brain. The measured activity is the proteolytic activity (DEVDase activity) of caspase-3 in CSF collected from patients with TBI.

Hanze (2001) evaluated the stability of caspase-3 in extracellular environment in vitro and in vivo after intravenous injection in mice. The measured activity is the proteolytic activity of caspase-3 using the DEVD artificial substrate. It was found that the plasma DEVDase activity decreased rapidly (T½=15 min.), but was still detectable after over 60 min. It was shown that caspase-3 like activity was released from cell lines exposed to apoptotic stimulus and that release of caspase occurs in pathological situations that are well characterized to have major involvement of classical apoptotic death. For example, DEVDase activity was present in plasma of a mice hepatitis model involving apoptotic liver damage. Also, elevated DEVDase activity was found in liquor of patients with traumatic brain injury. It has been proposed by Hantze et al. that the caspase enzymatic activity might serve as a diagnostic marker for massive apoptotic organ damage. Hantze et al. (2001) speculates that apart from being indicators of damage, extracellular caspases might in fact have defined targets in pathological situations and further stated that elucidation of such interactions remains a challenge for the understanding of fulminant apoptotic organ damage.

SUMMARY OF THE INVENTION

In one aspect, the invention relates to the use of a caspase, or a precursor, mutein, fused protein, functional derivative, active fraction, circularly permutated derivative or salt thereof in the manufacture of a medicament for treating and/or preventing a disease, disorder or condition causing death of cells.

In one embodiment of the invention, the cells and/or cells involved in removal of dead cells are responsive to regulation by extracellular caspase or by molecules which can be released by other cells or activated in response to extracellular caspase.

In a further embodiment of the invention, the regulation by extracellular caspase is manifested by the increase of nitric oxide (NO) level and/or production and/or secretion in the cells.

In another further embodiment of the invention, the cells are lymphocytes such as T lymphocytes and/or macrophages.

In another further embodiment of the invention, the caspase is selected from caspase-1, caspase-2, caspase-3, caspase-4, caspase-5, caspase-6, caspase-7, caspase-8, caspase-9, caspase-10, caspase-11, caspase-12, caspase-13 and caspase-14.

In certain embodiments of the invention, the caspase is caspase-8.

In another further embodiment of the invention, the disease, disorder or condition is selected from septic shock, acute hepatitis, graft versus host disease, AIDS, diabetes, and thyroiditis.

In another aspect, the invention relates to the use of a caspase, or a precursor, a mutein, fused protein, functional derivative, active fraction, circularly permutated derivative or salt thereof in the manufacture of a medicament for treating and/or preventing a disease, disorder or condition, wherein the pathogenesis or course of said disease disorder or condition is associated with cells that are responsive to regulation by extracellular caspase.

In one embodiment of the invention, the disease disorder or condition is associated with alterations in production and/or secretion levels of NO by the cells. For example, the caspase may increase production and/or secretion levels of NO by the cells.

In another embodiment of the invention, the disease disorder or condition is selected from sepsis, hepatitis, clotting events, angina pain, erectile dysfunction, hypercholesterolaemia, wound, and vascular inflammation.

In a further aspect, the invention relates to the use of a caspase, or a precursor, mutein, fused protein, functional derivative, active fraction, circularly permutated derivative or salt thereof in the manufacture of a medicament for treating and/or preventing a disease, disorder or condition, wherein the pathogenesis or course of said disease disorder or condition is associated with, or responsive to, alteration of the levels of NO.

In one embodiment of the invention, the disease disorder or condition is selected from septic shock, hepatitis, clotting events, angina pain, erectile dysfunction, hypercholesterolaemia, wound, and vascular inflammation.

In a further aspect, the invention relates to a caspase, or a precursor, mutein, fused protein, functional derivative, active fraction, circularly permutated derivative or salt thereof capable of acting extracellularly to regulate a cell function such as modulating the levels of NO produced and/or secreted by the cell.

In a further embodiment of the invention, the modulation is by increasing the levels of NO produced and/or secreted by the cell.

In a further embodiment of the invention, the cell is a macrophage.

In a further aspect, the invention relates to the use of a caspase, or a precursor, mutein, fused protein, functional derivative, active fraction, circularly permutated derivative or salt thereof capable of acting extracellularly to regulate a cell function, such as modulating the levels of NO produced and/or secreted by the cell, in the manufacture of a medicament.

In one embodiment of the invention, the medicament is used for treating and/or preventing a disease disorder or condition such as septic shock, hepatitis, clotting events, angina pain, erectile dysfunction, hypercholesterolaemia, wound, and vascular inflammation.

It is one object of the invention to provide the use of caspase-8 or a precursor, a mutein, fused protein, functional derivative, active fraction, circularly permutated derivative or salt thereof in the manufacture of a medicament for treating and/or preventing septic shock.

It is another object of the invention to provide the use of caspase-8 or a precursor, a mutein, fused protein, functional derivative, active fraction, circularly permutated derivative or salt thereof in the manufacture of a medicament for treating and/or preventing a disease disorder or condition such as hepatitis, clotting events, angina pain, erectile dysfunction, hypercholesterolaemia, wound, and vascular inflammation.

In one aspect of the invention, it is provided a pharmaceutical composition for treating and/or preventing a disease, disorder or condition causing death of cells comprising a caspase, or a precursor, mutein, fused protein, functional derivative, active fraction, circularly permutated derivative or salt thereof and a pharmaceutically acceptable carrier.

In one embodiment of the invention the disease, disorder or condition is selected from septic shock, acute hepatitis, graft versus host disease, AIDS, diabetes, and thyroiditis.

In another aspect, the invention relates to a pharmaceutical composition comprising a caspase, or a precursor, a mutein, fused protein, functional derivative, active fraction, circularly permutated derivative or salt thereof and a pharmaceutically acceptable carrier for treating and/or preventing a disease, disorder or condition, wherein the pathogenesis or course of said disease disorder or condition is associated with cells that are responsive to regulation by extracellular caspase.

In one embodiment, the disease disorder or condition selected from septic shock, hepatitis, clotting events, angina pain, erectile dysfunction, hypercholesterolaemia, wound, and vascular inflammation.

In one aspect, the invention provides a pharmaceutical composition comprising a caspase, or a precursor, a mutein, fused protein, functional derivative, active fraction, circularly permutated derivative or salt thereof, which is capable of acting extracellularly to regulate a cell function, and a pharmaceutically acceptable carrier.

In one embodiment of the invention, the disease disorder or condition selected from septic shock, hepatitis, clotting events, angina pain, erectile dysfunction, hypercholesterolaemia, wound, and vascular inflammation.

An additional object of the invention is to provide a pharmaceutical composition for treating and/or preventing septic shock comprising caspase-8 or a precursor, a mutein, fused protein, functional derivative, active fraction, circularly permutated derivative or salt thereof and a pharmaceutically acceptable carrier.

It is a further object of the invention to provide a pharmaceutical composition for treating a disease disorder or condition such as hepatitis, clotting events, angina pain, erectile dysfunction, hypercholesterolaemia, wound, and vascular inflammation, comprising caspase-8 or a precursor, a mutein, fused protein, functional derivative, active fraction, circularly permutated derivative or salt thereof and a pharmaceutically acceptable carrier.

In a further aspect, the invention provides a pharmaceutical composition comprising a caspase, or a precursor, a mutein, fused protein, functional derivative, active fraction, circularly permutated derivative or salt thereof and a pharmaceutically acceptable carrier for subcutaneous administration.

In another further aspect, the invention provides a pharmaceutical composition comprising a caspase, or a precursor, a mutein, fused protein, functional derivative, active fraction, circularly permutated derivative or salt thereof and a pharmaceutically acceptable carrier for systemic administration.

In another further aspect, the invention provides a pharmaceutical composition comprising a caspase, or a precursor, mutein, fused protein, functional derivative, active fraction, circularly permutated derivative or salt thereof and a pharmaceutically acceptable carrier for treating and/or preventing a disease, disorder or condition, wherein the pathogenesis or course of said disease disorder or condition is associated with, or responsive to, alteration of NO levels.

In one embodiment of the invention, the disease disorder or condition is selected from septic shock, hepatitis, clotting events, angina pain, erectile dysfunction, hypercholesterolaemia, wound, and vascular inflammation.

It is a further object of the invention to provide a pharmaceutical composition for treating and/or preventing a disease disorder or condition such as hepatitis, clotting events, angina pain, erectile dysfunction, hypercholesterolaemia, wound, and vascular inflammation, comprising caspase-8 or a precursor, a mutein, fused protein, functional derivative, active fraction, circularly permutated derivative or salt thereof and a pharmaceutically acceptable carrier.

It is a further object of the invention to provide a pharmaceutical composition comprising caspase-8, or a precursor, a mutein, fused protein, functional derivative, active fraction, circularly permutated derivative or salt thereof and a pharmaceutically acceptable carrier for subcutaneous administration.

It is a further object of the invention to provide a pharmaceutical composition comprising caspase-8, or a precursor, a mutein, fused protein, functional derivative, active fraction, circularly permutated derivative or salt thereof and a pharmaceutically acceptable carrier for systemic administration.

A further aspect of the invention relates to a method for treating and/or preventing a disease comprising administering in an individual in need a therapeutically effective amount of a caspase, or a precursor, a mutein, fused protein, functional derivative, active fraction, circularly permutated derivative or salt thereof which is capable of acting extracellularly to regulate a cell function, such as regulation of production and/or secretion levels of NO.

In one embodiment of the invention, the disease disorder or condition is selected from hepatitis, clotting events, angina pain, erectile dysfunction, hypercholesterolaemia, wound, and vascular inflammation.

Another aspect of the invention relates to a method of for treating and/or preventing a disease, disorder or condition causing death of cells, such as septic shock, acute hepatitis, graft versus host disease, AIDS, diabetes, and thyroiditis, comprising administering in an individual in need a therapeutically effective amount of a caspase, or a precursor, a mutein, fused protein, functional derivative, active fraction, circularly permutated derivative or salt thereof.

Another aspect of the invention relates to a method of for treating and/or preventing a disease, disorder or condition, wherein the pathogenesis or course of said disease disorder or condition is associated with cells that are responsive to regulation by extracellular caspase comprising administering in an individual in need a therapeutically effective amount of a caspase, or a precursor, a mutein, fused protein, functional derivative, active fraction, circularly permutated derivative or salt thereof.

In one embodiment of the invention, regulating a cell function involves modulation of levels of production and/or secretion of NO.

In a further embodiment of the invention, the disease disorder or condition is selected from hepatitis, clotting events, angina pain, erectile dysfunction, hypercholesterolaemia, wound, and vascular inflammation.

The invention provides a method of for treating and/or preventing a disease, disorder or condition, comprising administering in an individual in need a therapeutically effective amount of a caspase or a precursor, a mutein, fused protein, functional derivative, active fraction, circularly permutated derivative or salt thereof capable of acting extracellularly.

In addition, the invention provides a method of treating and/or preventing a disease, disorder or condition comprising subcutaneous administration of a caspase, or a precursor, a mutein, fused protein, functional derivative, active fraction, circularly permutated derivative or salt thereof in an individual in need.

In another aspect, the invention provides a method of treating and/or preventing a disease, disorder or condition comprising systemic administration of a caspase, or a precursor, a mutein, fused protein, functional derivative, active fraction, circularly permutated derivative or salt thereof in an individual in need.

It is one object of the invention to provide a method of treating and/or preventing a disease disorder or condition wherein the pathogenesis or course of said disease disorder or condition is associated with, or responsive to, alteration of NO levels, comprising administration of a caspase, or a precursor, a mutein, fused protein, functional derivative, active fraction, circularly permutated derivative or salt thereof in an individual in need.

In one embodiment of the invention, the disease disorder or condition is selected from sepsis, hepatitis, clotting events, angina pain, erectile dysfunction, hypercholesterolaemia, wound, and vascular inflammation.

DETAILED DESCRIPTION OF THE EMBODIMENTS

Figure 1A:
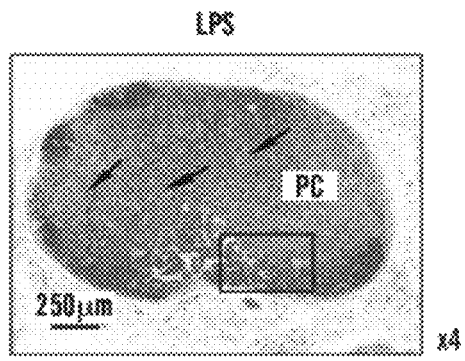
FIGS. 1A-1H show that subcutaneous (s.c.) injection of minute amounts of caspase-8 prevents accumulation of dead lymphocytes in a model of local inflammation mediated by lipopolysaccharide (LPS). The effect of s.c. caspase-8 administration on development of local inflammation mediated by s.c. and intraperitoneal (i.p.) injections of LPS was evaluated. In the experimental group, each mouse was injected s.c. with LPS (5 μg) alone and LPS (5 μg)+caspase-8 (16 ng) on the left and right side of the back, respectively, 24 hours later injected i.p. with LPS (50 μg), and 41-44 h after the first s.c. injection euthanized. In the control group, mice were treated with the s.c. and i.p. injections of LPS alone. The figures show longitudinal sections of samples from right inguinal lymph node located near the site of injection. The lymph nodes of control and experimental mice were stained with hematoxilin and eosine and analyzed at different magnification by light microscope. A, C, E, and G show samples obtained from mice injected with LPS alone and B, D, F, and H show samples obtained from mice injected with LPS and recombinant caspase-8. The cortex consists of paracortex (T cell area) and several primary follicles (B cell area). A and B show regions of the cortex and medulla of the lymph node (×4 magnification) (the medullar region is less defined in A). Multiple dark foci (some of which are marked with arrows) corresponding to dead lymphocytes that can be detected in the paracortex in A but not in B. C and D show higher magnification (×20) of the region including the paracortex and medullary sinuses, which is indicated by the squares in A and B, respectively. In C, dark foci of dead lymphocytes are marked with arrows, in D such foci are not defined. In both C and D cellular debris is present within the medullary sinuses (arrowheads). E and F show higher magnification (×100) of the paracortex region. The dark foci, two of which are circled in E, are composed of necrotic/apoptotic cellular debris. Smaller dark foci are infrequently found in F. G and H show higher magnification (×100) of medullary sinuses (MS). Clusters of necrotic cellular debris are marked with arrowheads. The necrotic cluster in H and the one on the right in G are intracytoplasmic, most probably within a macrophage.
Figure 1B:
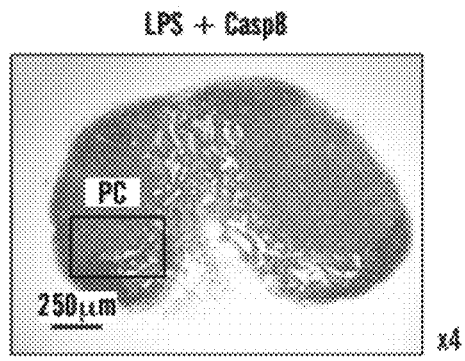
Figure 1C:
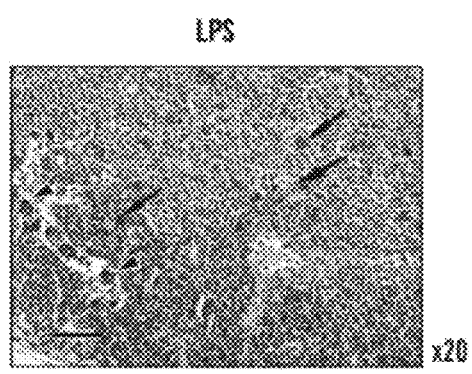
Figure 1D:
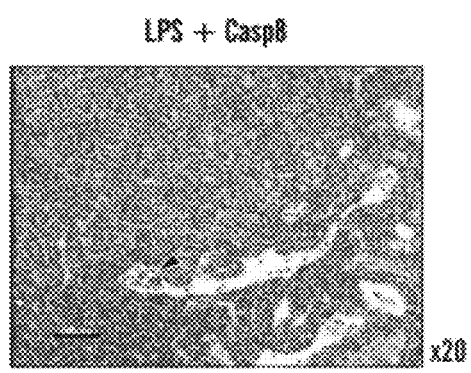
Figure 1E:
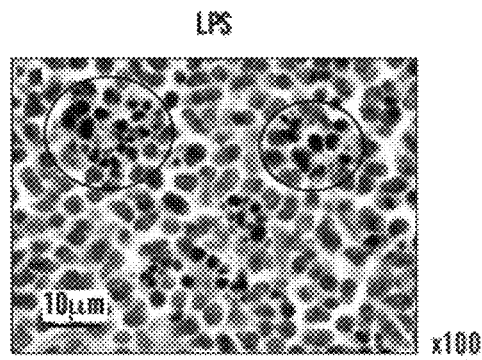
Figure 1F:
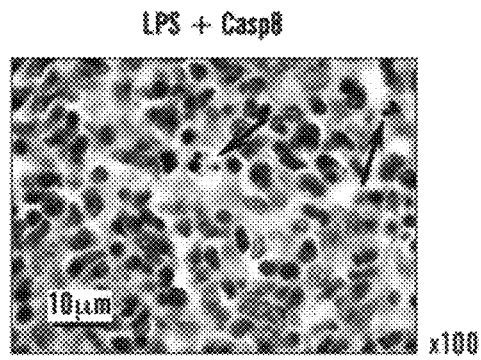
Figure 1G:
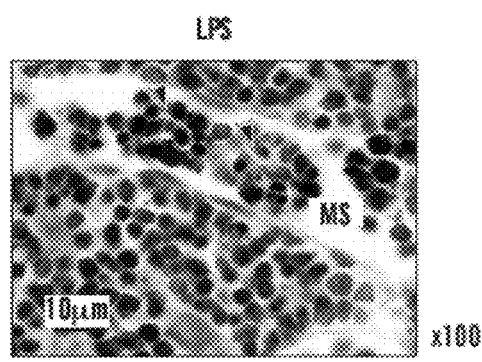
Figure 1H:
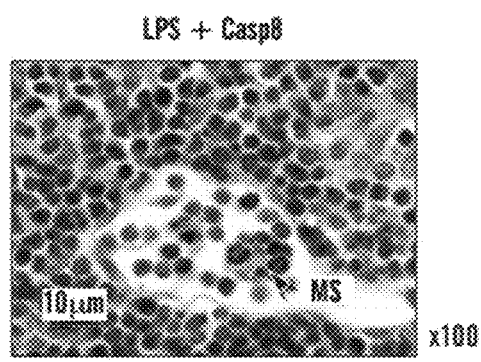
Figure 2A:
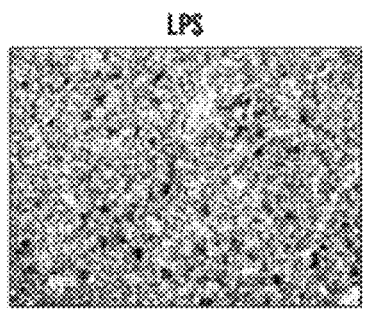
FIGS. 2A-2E show that s.c. LPS injections in the right and left sides of the back of the same mouse cause cell death in the paracortex of local inguinal lymph nodes. Samples of left and right lymph nodes obtained from 5 mice, each injected at the left and right sides of the back with LPS were stained, analyzed as in FIG. 1 (magnification·times·20) and compared. Each row, left and right, shows samples of left and right lymph nodes from the same mouse, respectively. Multiple dark foci corresponding to dead lymphocytes are detected in all samples.
Figure 2A:
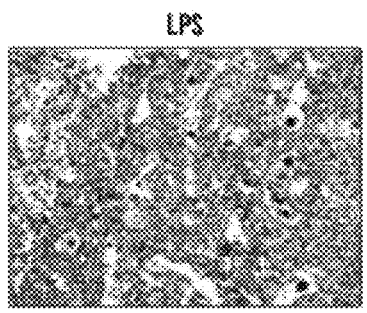
Figure 2B:
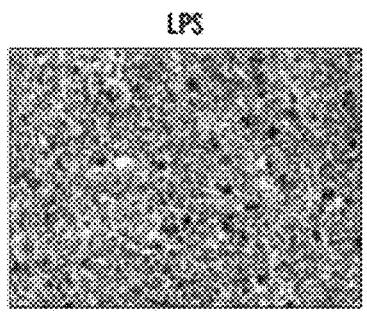
Figure 2B:
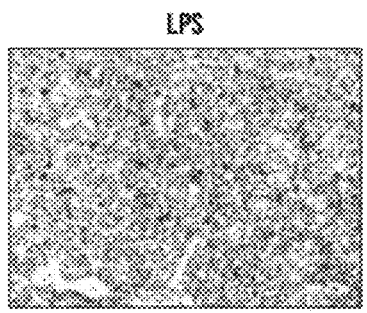
Figure 2C:
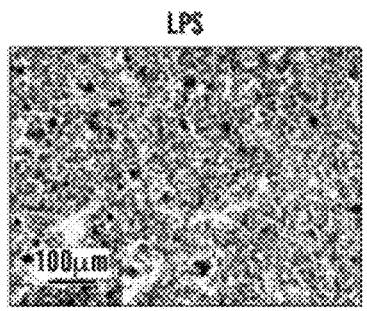
Figure 2C:
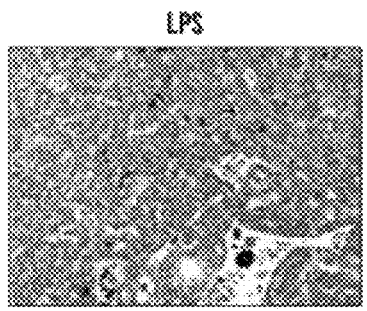
Figure 2D:
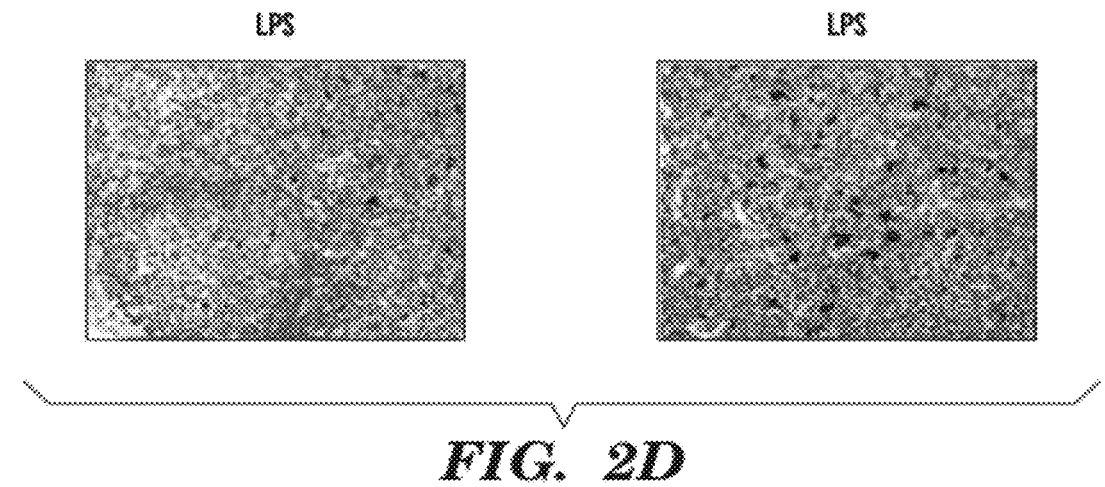
Figure 2E:
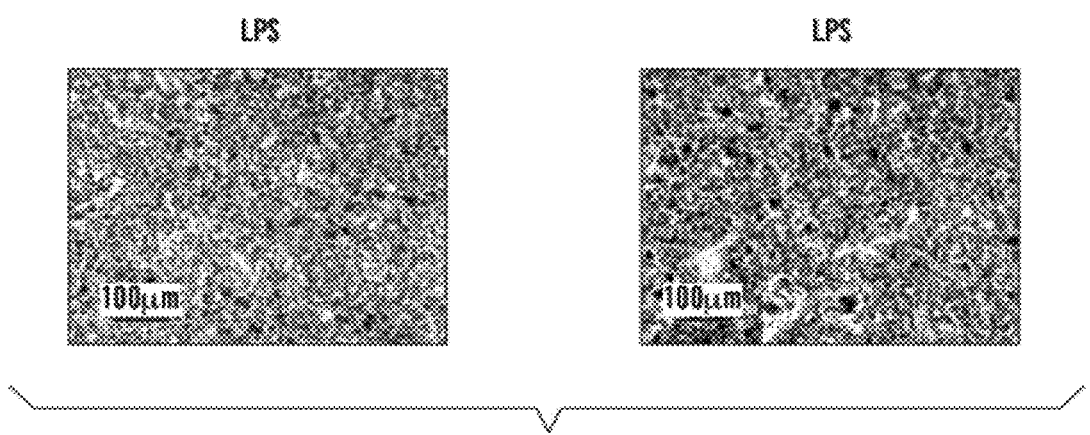
Figure 3A:
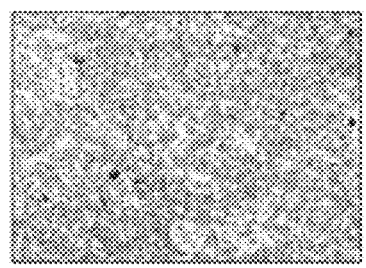
FIGS. 3A-3E show that the protective effect of caspase-8 in the model of local inflammation mediated by LPS is systemic. The figure shows samples of left and right side lymph nodes obtained from mice, each injected at the left and right sides of the back with LPS and co-injected at the right side with caspase-8, stained, analyzed (magnification ·times·20) as in FIG. 1 and compared. Each row, left and right, shows samples of left and right lymph nodes from the same mouse, respectively. This experiment has been carried out with 15 mice, the present figure shows 5 representative mice. Dark foci were rarely found in samples from lymph node of the right and left side of each animal, i.e. close and far from the caspase-8 injection, respectively. Since the protective effect of caspase-8 was not restricted to the lymph node adjacent to caspase-8 injection, this effect is systemic.
Figure 3A:
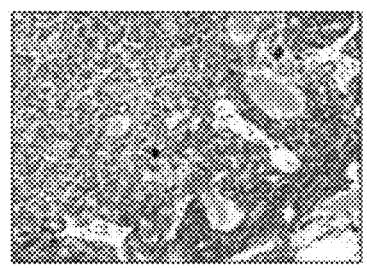
Figure 3B:
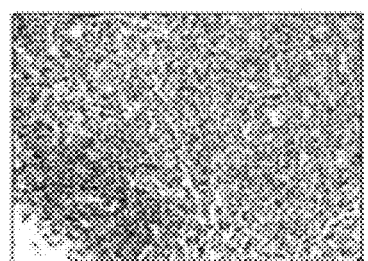
Figure 3B:
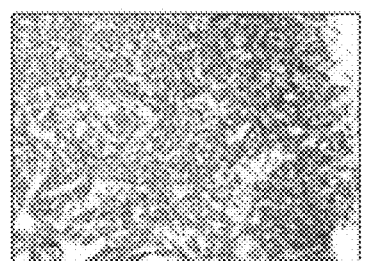
Figure 3C:
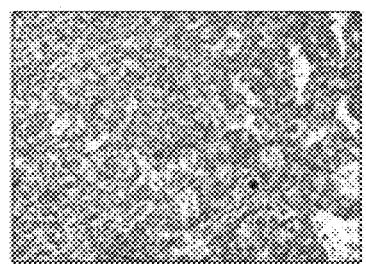
Figure 3C:
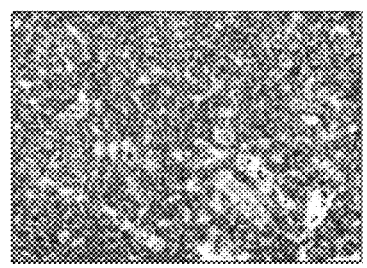
Figure 3D:
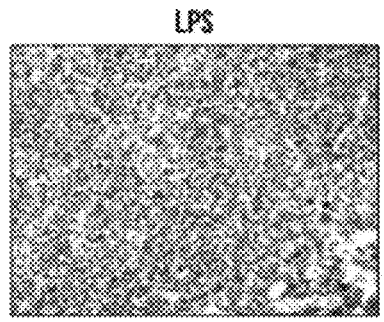
Figure 3D:
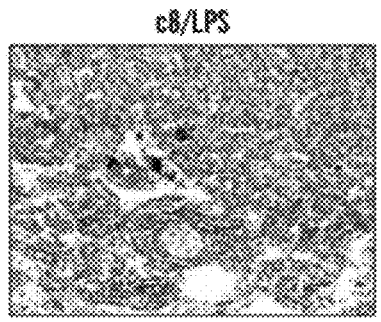
Figure 3E:
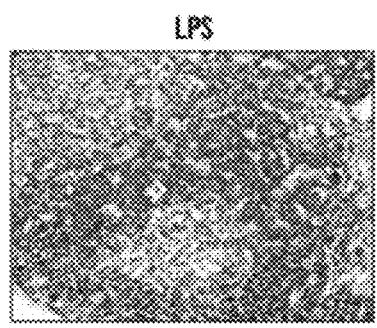
Figure 3E:
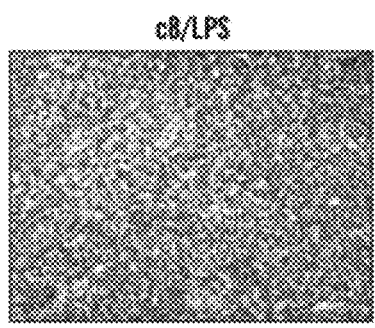

In one aspect, the invention relates to the use of a caspase, or a mutein, fused protein, functional derivative, active fraction, circularly permutated derivative or salt thereof in the manufacture of a medicament for treating and/or preventing a disease, disorder or condition causing death of cells.

Caspases are known to act intracellularly and to be required for execution of cell death (apoptosis). Differently from the known role of intracellular caspases as inducer or facilitator of apoptosis and from the reports favouring blocking caspases in order to alleviate diseases involving massive death of cells, we show herein the surprising results that administration of a caspase, such caspase-8, attenuates LPS mediated lymphocyte death and/or accumulation of dead lymphocytes in an animal model. The in vivo results obtained herein, suggest that caspases may act extracellularly and that the extracellular activity of caspases may differ from their known intracellular one.

In view of our findings showing that a single s.c. injection with minute amounts of caspase-8 had, not only local but, a systemic beneficial effect in the animal model, a possibility exists that extracellular caspase-8 has a cytokine-like activity and that a signal is transduced upon binding of the caspase to a particular receptor present in certain responsive cells.

While the intracellularly mediated pro-apoptotic role of caspases requires the proteolytic activity of the caspases, the extracellular role of caspases may be independent of such activity. Therefore, a caspase, or a mutein, fused protein, functional derivative, active fraction, circularly permutated derivative or salt thereof lacking proteolytic activity or inactive pro-enzyme precursor is also contemplated as useful in practicing the present invention.

It is possible that the arrest of lymphocyte death or attenuated accumulation of dead lymphocytes observed in the animal model administered with the caspase is caused by a direct effect of the injected caspase on the dying cells and/or on cells required for removing dying cells (e.g. macrophages). Nevertheless, it is also possible that the effect of the caspase is an indirect one. For example, caspase-8 may induce release of some other mediators by other cells, which are the actual direct target of the caspase and/or may generate a mediator as a consequence of an effect of the caspase on some components of the serum, extracellular matrix or cell-surface protein. These mediators may in turn act on the dying cells and/or on cells required for removing dying cells. Thus the extracellular action of caspase-8 may inhibit directly or indirectly the death of lymphocytes and/or enhance the activity of cells required for removing death cells.

Examples of diseases disorders or conditions causing/associated with massive death of cells or unregulated death of cells, include, but are not limited to septic shock, acute hepatitis, graft versus host disease, AIDS, diabetes, and thyroiditis.

Example of a caspase according to the invention include, but is not limited to, caspase-1, caspase-2, caspase-3, caspase-4, caspase-5, caspase-6, caspase-7, caspase-8, caspase-9, caspase-10, caspase-11, caspase-12, caspase-13 and caspase-14.

Preventing lymphocyte apoptosis or accumulation of dead lymphocytes by administration of a caspase, such as caspase-8, represents a potential important new therapy in septic shock.

In certain embodiments, the invention provides the use of caspase-8, pro-enzyme precursor of caspase-8, or a mutein, fused protein, functional derivative, active fraction, circularly permutated derivative or salt thereof (referred herein as "a substance according to the invention") in the manufacture of a medicament for treating and/or preventing septic shock.

U.S. Pat. Nos. 6,399,327 and 6,586,571, of the present applicant, disclose inter alia the caspase-8 protein and DNA, intracellular protease activity of Caspase-8 (or as previously designated, MACH), the binding of caspase-8 to the protein MORT-1 (or FADD), and the role of caspase-8 in cell-death induction.

As mentioned in the background of the invention, the release of activated caspases from apoptotic cells was reported to occur in pathological situations that are characterized to be associated with classical apoptotic death. These reports provide information only on the situations in which extracellular caspases occur and raise speculation just of a prejudicial effect of the extracellular proteolytic activity of caspase-3.

The results obtained herein show for the first time that caspases, such as caspase-8, can be used extracellulary to attenuate cell death and/or reduce accumulation of dead cells in a disease disorder or condition causing death of cells.

We carried out in vitro experiments to explore the direct effect of extracellular activity of caspases on cells. We found that incubation of caspase-8 with primary macrophages changes the rate of nitric oxide (NO) generation by these cells. This finding demonstrates that extracellular caspase has a direct effect in macrophage cells. Thus, the results obtained herein show that caspases such as caspase-8 can be used extracellulary for regulating a cell function.

In one example we show that addition of recombinant caspase-8 to the culture medium of peritoneal macrophages induced the secretion of NO. Secretion of NO by macrophages continued after changing the medium and removal of caspase-8. 48 hours after induction with caspase-8, the level of secreted NO was four times higher than the levels of NO after 24 h of caspase-8 induction. The levels of secreted NO were comparable to those induced by activation of macrophages by LPS. Low doses of LPS, which failed to stimulate NO secretion, slightly increased NO secretion mediated by caspase-8. We also demonstrated herein that, unlike LPS treatment, and unlike intracellular caspase-8, extracellular caspase-8 was not cytotoxic to the cells.

The findings herein show that extracellular caspase can modulate several cellular functions by affecting NO secretion and/or production levels in responsive cells. Thus in one aspect of the invention, a caspase, a pro-enzyme, or a mutein, fused protein, functional derivative, active fraction, circularly permutated derivative or salt thereof is used in the manufacture of a medicament for treating and/or preventing a disease, disorder or condition that is associated with cells responsive to regulation by extracellular caspase. In another aspect of the invention, a caspase, a pro-enzyme, or a mutein, fused protein, functional derivative, active fraction, circularly permutated derivative or salt thereof is used in the manufacture of a medicament for treating and/or preventing a disease disorder or condition wherein the pathology or the course of said disease disorder or condition is associated with alterations in NO levels or is responsive to alterations in NO levels.

NO is synthesized in cells by NO synthase (NOS). The human (and mouse) genome contains 3 different genes encoding NO synthases (nNOS found in neurons, eNOS found in the endothelial cells, and iNOS found in macrophages). The levels of nNOS and eNOS are relatively steady, and expression of iNOS genes are modulated by appropriate stimulus. All types of NOS produce NO from arginine with the aid of molecular oxygen and NADPH. Early reports show that NO regulates vasodilatation (Palmer R M, 1987), neurotransmition (Garthwaite, 1991) and immunological processes (Nathan 1991).

NO can exert beneficial or detrimental effect depending on the physiopathological context. Thus, in some cases it is desired to prevent NO production while in other cases it is desired to deliver or increase NO production.

For example, a caspase, or a precursor, mutein, fused protein, functional derivative, active fraction, circularly permutated derivative or salt thereof can be used in a disease disorder or condition associated with decreased NO levels and/or in a disease disorder or condition known to be ameliorated by increasing NO levels.

An inhibitor of the extracellular activity of a caspase can be used in a disease disorder or condition associated with the increase of NO levels and/or in a disease disorder or condition known to be ameliorated by decreasing NO levels. A particular fragment of a caspase may turn to have dominant negative effect of the extracellular function of the caspase and may be used to decrease NO production/secretion levels.

Examples of a disease disorder or condition in which the pathology or the course of the diseases disorder or condition is associated with alteration in NO levels or is responsive to NO levels include, but is not limited to; chronic neurodegenerative diseases such as Parkinson's disease (Shavali et al. 2006, Salerno 2002, Ebadi and Sharma 2003), schizophrenia (Salerno 2002), Alzheimer (Salerno 2002) and AII dementia (Salerno 2002)]; artherosclerosis (Sun et al. 2005); stroke (Salerno et al. 2002); acute ischemic stroke (Willmot); chronic convulsions (Salerno et al. 2002); chronic pain (Salerno et al. 2002); chronic tension-type headache (Ashina 2002); optic neuropathy (Neufeld 2004); hepatic injury (Chen 2003); wound (Childress, 2002, Park, 2004); erectile dysfunction (Toda, 2004); inflammatory diseases such as colitis (Ballester et al. 2005); cardiac inflammation (Bradford et al. 2001); and glomerular disease (Mattana et al. 1998).

Neufeld (2004) reported that excessive NO, generated in astrocytes and microglia in the optic nerve head of patients with glaucoma might contribute to the optic neuropathy associated with the disease, and indicated that inhibitors of NO production can be used in the disease.

Chen et al. (2003) indicated that NO potentiates the hepatic oxidative injury in warm ischemia/reperfusion of the liver, while iNOS expression protects against hepatic apoptotic cell death seen in models of sepsis and hepatitis. Chen et al (2003) point out that whether NO protects or injures is probably determined by the type of insult, the abundance of reactive oxygen species, the source and amount of NO production and the redox status of the liver.

Nitric oxide has been used as a therapeutic tool to treat diseases that range from recurrent narrowing of arteries to inhibiting clotting events. Many commonly used medications have their therapeutic actions through the production of nitric oxide. Therefore, a caspase, or a precursor, mutein, fused protein, functional derivative, active fraction, circularly permutated derivative or salt thereof can be used to increase nitric oxide levels and inhibit clotting events.

NO relaxes the smooth muscle in the walls of the arterioles. At each systole, the endothelial cells that line the blood vessels release a puff of NO. This diffuses into the underlying smooth muscle cells causing them to relax and thus permit the surge of blood to pass through easily. Mice whose gene for eNOS has been "knocked out" suffer from hypertension. Nitroglycerine, which is often prescribed to reduce the pain of angina, does so by generating nitric oxide, which relaxes the walls of the coronary arteries and arterioles. Nitric oxide leads to relaxation of blood vessels, regeneration of the endothelium, and inhibition of platelet clumping which makes the blood thinner. Therefore, a caspase, or a precursor, mutein, fused protein, functional derivative, active fraction, circularly permutated derivative or salt thereof can be used to increase nitric oxide and reduce the pain of angina.

One of the main physiological causes of impotence, or erectile dysfunction, is inability of the blood vessels in the penis to dilate enough to allow blood flow and engorgement. Erectile dysfunction (ED) is caused by a variety of pathogenic factors, particularly impaired formation and action of NO. Thus, replenishment of this molecule is expected so far to be the most promising therapeutic measures for patients with ED. (Toda et al. 2005). Therefore, a caspase, or a precursor, mutein, fused protein, functional derivative, active fraction, circularly permutated derivative or salt thereof can be used to increase nitric oxide level for treatment of erectile dysfunction.

Oxidised LDL is proatheromatic, and toxic peroxidation products contribute to further endothelial damage. NO controls vascular tone, inhibits LDL oxidation and has hypocholesterolaemic activity (Rekka 2002). Therefore, a caspase, or a precursor, mutein, fused protein, functional derivative, active fraction, circularly permutated derivative or salt thereof can be used to increase nitric oxide and reduce hypercholesterolaemia.

The beneficial role of NO in wound healing has been reviewed by Childress (2002) and Park (2004). Therefore, a caspase, or a precursor, mutein, fused protein, functional derivative, active fraction, circularly permutated derivative or salt thereof can be used to increase nitric oxide to facilitate wound healing.

Nitric oxide may regulate exocytosis in a variety of diseases. Regulated exocytosis and the release of bioactive molecules are essential events in physiological processes such as neurotransmission, the immune response to microbial infections, wound healing, and the control of the blood glucose level. Exocytosis involves the controlled fusion of mediator-containing storage granules with the plasma membrane. NO inhibits exocytosis in endothelial cells causing nitrosylation of NSF (N-ethylmaleimide-sensitive factor). NSF is a protein responsible for membrane trafficking and exocytosis (Matsushita, et al., 2003). NO may regulate exocytosis in a variety of physiological processes, including vascular inflammation, neurotransmission, thrombosis, and cytotoxic T lymphocyte cell killing. Nitric oxide (NO) inhibits vascular inflammation and the mechanism involved in this antiinflammatory activity appears to be NO regulated exocytosis Matsushita, et al., Cell, 2003. Therefore, a caspase, or a precursor, mutein, fused protein, functional derivative, active fraction, circularly permutated derivative or salt thereof can be used to increase nitric oxide and reduce vascular inflammation.

In another aspect, the invention relates also to a caspase pro-enzyme, or mutein, fused protein, functional derivative, active fraction, circularly or permutated derivative lacking the proteolytic activity and capable of acting extracellularly to regulate a cell function.

One object of the invention is to provide pharmaceutical compositions comprising a caspase pro-enzyme, or a mutein, fused protein, functional derivative, active fraction, circularly or permutated derivative lacking the proteolytic activity and capable of acting extracellularly to regulate a cell function, and a pharmaceutically acceptable carrier.

As used herein the term "muteins" refers to analogs of a protein, in which one or more of the amino acid residues of the naturally occurring components of the protein are replaced by different amino acid residues, or are deleted, or one or more amino acid residues are added to the original sequence of the protein, without changing considerably the activity of the resulting products as compared with the original protein. These muteins are prepared by known synthesis and/or by site-directed mutagenesis techniques, or any other known technique suitable therefore.

Muteins in accordance with the present invention include proteins encoded by a nucleic acid, such as DNA or RNA, which hybridizes to DNA or RNA, which encodes the protein, in accordance with the present invention, under stringent conditions. The term "stringent conditions" refers to hybridization and subsequent washing conditions, which those of ordinary skill in the art conventionally refer to as "stringent". See Ausubel et al., Current Protocols in Molecular Biology, supra, Interscience, N.Y., §§6.3 and 6.4 (1987, 1992), and Sambrook et al. (Sambrook, J. C., Fritsch, E. P., and Maniatis, T. (1989) Molecular Cloning: A Laboratory Manual, Cold Spring Harbor Laboratory Press, Cold Spring Harbor, N.Y.).

Without limitation, examples of stringent conditions include washing conditions 12°-20° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30-60 minutes and then, a 0.1× SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC. See Ausubel, supra.

Any such mutein preferably has a sequence of amino acids sufficiently duplicative of that of the caspase, such as to have substantially similar, or even better, extracellular activity. For example, one extracellular activity of the caspase is the capability of causing an effect on the function of a cell. For example, incubating macrophages with the caspase induces NO production in these cells. An assay for measuring NO secretion to the medium, is described in the examples below. Another activity of the caspase is to attenuate LPS mediated lymphocyte death or accumulation of dead cells as described in the animal model in the examples below. As long as the mutein is capable to have substantial activity, such as induction of NO production in macrophages, and/or attenuation of dead lymphocyte accumulation in an animal model for a disease causing massive or unregulated death of lymphocytes, it can be considered to have substantially similar activity to the caspase. Thus, it can be determined whether any given mutein has at least substantially the same activity as the caspase of the present invention by means of routine experimentation as shown for caspase-8 in the examples below.

In a preferred embodiment, any such mutein has at least 40% identity or homology with the amino acid sequence of the caspase. More preferably, it has at least 50%, at least 60%, at least 70%, at least 80% or, most preferably, at least 90% identity or homology thereto.

Identity reflects a relationship between two or more polypeptide sequences or two or more polynucleotide sequences, determined by comparing the sequences. In general, identity refers to an exact nucleotide-to-nucleotide or amino acid to amino acid correspondence of the two polynucleotide or two polypeptide sequences, respectively, over the length of the sequences being compared.

For sequences where there is not an exact correspondence, a "percent identity" may be determined. In general, the two sequences to be compared are aligned to give a maximum correlation between the sequences. This may include inserting "gaps" in either one or both sequences, to enhance the degree of alignment. A percent identity may be determined over the whole length of each of the sequences being compared (so-called global alignment), that is particularly suitable for sequences of the same or very similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux J et al 1984, Nucleic Acids Res. 1984 Jan. 11; 12(1 Pt 1): 387-95), for example the programs BESTFIT and GAP, may be used to determine the % identity between two polynucleotide and the % identity and the % homology between two polypeptide sequences. BESTFIT uses the "local homology" algorithm of Smith and Waterman (J Theor Biol. 1981 Jul. 21; 91(2):379-80 and J Mol. Biol. 1981 Mar. 25; 147(1):195-7. 1981) and finds the best single region of similarity between two sequences. Other programs for determining identity and/or similarity between sequences are also known in the art, for instance the BLAST family of programs (Altschul S F et al, 1990 J Mol. Biol. 1990 Oct. 5; 215(3):403-10, Proc Natl Acad Sci USA. 1990 July; 87(14):5509-13, Altschul S F et al, Nucleic Acids Res. 1997 Sep. 1; 25(17):3389402, accessible through the home page of the NCBI at www.ncbi.nlm.nih.gov) and FASTA (Pearson W R, Methods Enzymol. 1990; 183:63-98. Pearson J Mol. Biol. 1998 Feb. 13; 276(1):71-84).

Muteins of the caspase, which can be used in accordance with the present invention include a finite set of substantially corresponding sequences as substitution peptides or polynucleotides which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of the caspase may include synonymous amino acids within a group which have sufficiently similar physicochemical properties that substitution between members of the group will preserve the biological function of the molecule (Grantham Science. 1974 Sep. 6; 185(4154):862-4). It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the purview of the present invention.

Examples of production of amino acid substitutions in proteins which can be used for obtaining muteins of the caspase, for use in the present invention include any known method steps, such as presented in U.S. Pat. Nos. 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Shaw et al).

"Functional derivatives" as used herein cover derivatives of the caspase, and their muteins, which may be prepared from the functional groups which occur as side chains on the residues or are additions to the N- or C-terminal groups, by means known in the art, and are included in the invention as long as they remain pharmaceutically acceptable, i.e. they do not destroy the activity of the protein which is substantially similar to the activity of the caspase.

"Functional derivatives" also comprise multimers made up of the caspase in which changes have been introduced in the sequence of the amino acids making up the caspase by any conventional method. These changes may comprise elongation or truncation of the caspase molecule or deletion or replacement of one or more amino acids of the caspase. It is understood that none of the above changes may affect the properties of the caspase.

These derivatives may, for example, include polyethylene glycol side-chains, which may mask antigenic sites and extend the residence of the caspase in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carboxylic aroyl groups) or O-acyl derivatives of free hydroxyl groups (for example that of seryl or threonyl residues) formed with acyl moieties.

As long as the functional derivatives is capable to have substantial activity or properties, such as induction of NO production in macrophages, and/or attenuation of dead lymphocytes accumulation in an animal model, it can be considered to have substantially similar activity to the caspase or similar properties to the caspase.

An "active fraction" according to the present invention may e.g. be a fragment of the caspase. The term fragment refers to any subset of the molecule, that is, a shorter peptide that retains the desired biological activity of the caspase. Fragments may readily be prepared by removing amino acids from either end of the caspase and testing the resultant fragment for its activity in macrophages and/or in the model of local inflammation. Proteases for removing one amino acid at a time from either the N-terminal or the C-terminal of a polypeptide are known, and so determining fragments, which retain the desired biological activity, involves only routine experimentation.

As active fractions of the caspase, muteins and fused proteins thereof, the present invention further covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has substantially similar activity to the caspase.

As long as the active fraction or the fragment is capable to have substantial activity, such as induction of NO production in macrophages, and/or attenuation of dead lymphocyte accumulation in an animal model, it can be considered to have substantially similar activity to the caspase or similar properties to the caspase.

The term "fused protein" refers to a polypeptide comprising a caspase, or a mutein or fragment thereof, fused with another protein, which, e.g., has an extended residence time in body fluids. A caspase may thus be fused to e.g., an immunoglobulin or a fragment thereof.

"Isoforms" of caspase are proteins capable of having the caspase activity or fragment thereof, which may be produced by alternative splicing.

The term "circularly permuted derivatives" as used herein refers to a linear molecule in which the termini have been joined together, either directly or through a linker, to produce a circular molecule, and then the circular molecule is opened at another location to produce a new linear molecule with termini different from the termini in the original molecule. Circular permutations include those molecules whose structure is equivalent to a molecule that has been circularized and then opened. Thus, a circularly permuted molecule may be synthesized de novo as a linear molecule and never go through a circularization and opening step. The preparation of circularly permutated derivatives is described in WO95/27732.

The term "salts" herein refers to both salts of carboxyl groups and to acid addition salts of amino groups of the caspase. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of the caspase.

As long as the caspase isoform, or circularly permuted derivative or salts thereof is capable to have substantial activity, such as induction of NO production in macrophages, and/or attenuation of dead lymphocyte accumulation in an animal model, it can be considered to have substantially similar activity to the caspase or similar properties to the caspase.

The terms "treating/ameliorating" used herein should be understood as preventing, inhibiting, attenuating, ameliorating or reversing one or more symptoms or cause (s) of the disease disorder or condition. When "treating/ameliorating", a substance according to the invention is given after onset of the disease disorder or condition, "prevention" relates to administration of the substances before any signs of disease disorder or condition can be noted in the patient.

Preventive administration is especially useful in patients having high-risk to be ill or suffer from the disease disorder or condition.

It is a further object of the present invention to provide for a method for treating and/or preventing sepsis, comprising administering to a patient in need thereof a dose of caspase-8, a mutein, fused protein, functional derivative, active fraction, circularly permutated derivative or salt thereof optionally together with a pharmaceutically acceptable carrier.

A further object of the present invention is to provide a pharmaceutical composition comprising a substance according to the invention and a pharmaceutically acceptable carrier. The pharmaceutical composition according to the present invention includes a sufficient amount of caspase-8 to achieve its intended purpose. In addition, the pharmaceutical compositions may contain suitable pharmaceutically acceptable carriers comprising excipients and auxiliaries, which facilitate processing of the active compounds into preparations which can be used pharmaceutically and which can stabilize such preparations for administration to the subject in need thereof as well known to those of skill in the art.

The substance can be administered to a patient in need thereof in a variety of ways. The routes of administration include intraliver, intradermal, transdermal (e.g. in slow release formulations), intramuscular, intraperitoneal, intravenous, subcutaneous, oral, epidural, topical, and intranasal routes. In addition the substance can be administered together with other components of biologically active agents such as pharmaceutically acceptable surfactants, excipients, carriers, diluents and vehicles.

For parenteral (e.g. intravenous, subcutaneous, intramuscular) administration, caspase-8 can be formulated as a solution, suspension, emulsion or lyophilized powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

We have shown herein that subcutaneous injection of caspase-8 is suitable for systemic treatment. Therefore, in one embodiment of the invention, caspase-8 is subcutaneously administered, preferably for systemic treatment.

The dosage administered, as single or multiple doses, to an individual will vary depending upon a variety of factors, including the substance pharmacokinetic properties, the route of administration, patient conditions and characteristics (sex, age, body weight, health, size), extent of symptoms, concurrent treatments, frequency of treatment and the effect desired. Adjustment and manipulation of established dosage ranges are well within the ability of those skilled.

The definition of "pharmaceutically acceptable" is meant to encompass any carrier, which does not interfere with effectiveness of the biological activity of the active ingredient and that is not toxic to the host to which it is administered. For example, for parenteral administration, the substance according to the invention may be formulated in a unit dosage form for injection in vehicles such as saline, dextrose solution, serum albumin and Ringer's solution.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy. Optimum dose levels and frequency of dosing will be determined by clinical trial.

The compounds with which the invention is concerned may be prepared for administration by any route consistent with their pharmacokinetic properties.

The orally administrable compositions may be in the form of tablets, capsules, powders, granules, lozenges, and liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia;

Non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations, which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non-aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such ashypromellose may also be included.

The active ingredient may also be administered parenterally in a sterile medium. Depending on the vehicle and concentration used, the drug can either be suspended or dissolved in the vehicle. Advantageously, adjuvants such as local anaesthetic, preservative and buffering agents can be dissolved in the vehicle.

The term "dosage" relates to the determination and regulation of the frequency and number of doses.

Having now fully described this invention, it will be appreciated by those skilled in the art that the same can be performed within a wide range of equivalent parameters, concentrations and conditions without departing from the spirit and scope of the invention and without undue experimentation.

All references cited herein, including journal articles or abstracts, published or unpublished U.S. or foreign patent application, issued U.S. or foreign patents or any other references, are entirely incorporated by reference herein.

Reference to known method steps, conventional methods steps, known methods or conventional methods is not any way an admission that any aspect, description or embodiment of the present invention is disclosed, taught or suggested in the relevant art.

The present invention will now be described in more detail in the following non-limiting examples and the accompanying drawings.

EXAMPLES

The effect of subcutaneous (s.c.) administration of caspase-8 in development of LPS mediated inflammation was examined in an animal model.

The extracellular effect of caspase-8 was assessed in vitro employing a culture of primary peritoneal macrophages.

Material and Methods:

Administration of mice with LPS and/or caspase-8. All studies were carried out in accordance with Weizmann Institute of Science Guidelines on Laboratory Animals and were approved by the Weizmann Institute of Science Committee on Animal Use and Care. Six to seven-week old BALB/C OLA males mouse (of about 16-21 gram) were shaved at the right and left sides of their back. In the experimental group, 16 ng recombinant human caspase-8 (100 µl out of a stock of 160 ng caspase-8/ml PBS endotoxin free) and 5 µg $E.$ $coli$ lipopolysaccharide (LPS) dissolved in 50 µl PBS were injected subcutaneously (s.c.) to the right side of the back of a mice. The same dose of LPS, but without caspase-8, was injected subcutaneously to the left side of the back of the same mice. 24 hours later 50 µg of LPS dissolved in 500 µl PBS was injected intraperitonealy (i.p.) in a total volume of 500 µl PBS. 17-20 h after the i.p. injection, or 41-44 h after the first s.c. injection, mice were euthanized by $CO_2$. In the control group mice were treated with both s.c. injections and one i.p. injection of LPS only.

Recombinant and purified active human caspase-8 produced in $E.$ $coli$ (Serono) was used for injection. Prior to use, caspase-8 was pre-treated with polymixin B-agarose (Sigma) at 40° C. for 15 minutes, to remove any possible traces of LPS, and then sterilized by filtration through 0.2 um mesh filter.

LPS from $E.$ $coli$ 0111-B4, and PBS endotoxin free that were used in the experiments were purchased from Sigma.

The experiment were carried out twice:

In the first experiment: the experimental group included 10 mice and the control group 5 mice; in the second experiment: both, the experimental and control group included 5 mice.

The skin at the site of injection was examined macroscopically and microscopically for signs of inflammation. In the subcutis, there is local neutrophilic infiltration. An infiltrate of similar composition is present in the dermis where it is multifocal and mild. Many of the infiltrating neutrophils are degenerate and necrotic/apoptotic. In some mice in the infiltrated area is edema, congestion, multifocal acute hemorrhage. Histologic diagnosis: locally extensive acute neutrophilic and hemorrhagic cellulites and dermatitis. The similar picture was observed in both groups of mice. Local inguinal lymph nodes were examined by histochemistry analysis. Inguinal lymph nodes were isolated from fat tissue under the binocular, and fixed over night in 10% phosphate buffered formaline at room temperature. Parafin sections of fixed tissue were stained with hematoxilin and eosine (Routine Mater's hematoxylin and eosin stain. Manual of Histologic Staining Methods of the Armed Forces Institute of Pathology (Third Edition). American Registry of Pathology (Luna, Lee G., HT (ASCP) (editor)), McGraw Hill Publishers, New York 1960.

Preparation of cultures of primary peritoneal macrophages. C57/Black males of 12-14 week old were injected intraperitoneally with 2 ml of 3% Thyoglycolate (Difco). 4 days latter mice were euthanized and cells enriched with peritoneal macrophages were collected by lavage with 10 ml of ice-cold PBS twice. Residual erythrocytes, which were present in the collected cells, were eliminated by lysis on ACK buffer (ACK buffer: 4.13 g Ammonium Chloride (NH4Cl); 0.5 g KHCO3; 18.5 mg Na4EDTA; Mess up to 500 ml with double distilled water.)

Remaining cells were seeded in DMEM with 5% FCS, 1 mM sodium pyruvate, 1 mM HEPES, and 50 uM b-mercaptoethanol. A stock solution comprising $3.2 \times 10^6$/ml cells was prepared and samples of 100 µl were seeded per well in 96-well plates. 2 h after seeding, non-adherent cells were washed away and the bound cells representing the culture of primary peritoneal macrophage were supplemented with medium.

Treatment of cultures of peritoneal macrophage with LPS or caspase-8. Primary cultures of peritoneal macrophage in 96-well plates were incubated for 21-24 h with medium supplemented with different concentrations of LPS (0, 0.01, 0.1 and 1 µg/ml) and/or caspase-8 (0, 0.8, 1.6 and 3.2 µg/ml), in triplicates. Next, the medium was collected for evaluation of NO secretion, and the wells were re-filled with fresh medium lacking LPS or caspase-8 for additional time. Then, the medium was collected again for NO evaluation. Before application to the cells, caspase-8 was diluted in PBS.

Survival of cells. Survival of cells under LPS or caspase-8 treatment was examined by staining with neutral red.

Evaluation of NO. The amount of NO secreted by macrophages was measured using Greiss procedure, as described previously by Fleming et al. (Fleming S D, Campbell P A. Macrophages have cell surface IL10 that regulates macrophage bactericidal activity. J. Immunol, 1996, v. 156: 1143-1150). Briefly, 50 µl of the cell free supernatant was added to 50 µl Greiss reagent (Sigma) and mixed by pipetation. OD550 was read with an ELISA reader.

Example 1

Protective Effect of Subcutaneous Administration of Caspase-8 in an Animal Model of Local Inflammation Induced by LPS (Scwartzmann Reaction)

LPS administration was reported to mediate massive lymphocyte apoptosis in lymph nodes from injected mice (Castro et al. 1998). The effect of caspase-8 administration in LPS mediated death of lymphocytes was assessed in vivo. In the experimental group, each mouse was injected twice s.c. (1) with LPS (5 µg)+caspase-8 (16 ng) and (2) with LPS (5 µg) alone on the right and left side of the back, respectively, and 24 hours later injected with LPS (50 µg) i.p. 41-44 h after the first s.c. injection the mouse was euthanized. In the control group mice were treated with the s.c. and i.p. injections of LPS alone (for details see the materials and methods section). Samples consisting of sections of inguinal lymph nodes located near the site of injection were examined. Lymph nodes are composed of cortex and medullar zones. The cortex consists of the paracortex (PC) region, which is populated mainly with T cells and follicular zone containing predominantly B-lineage lymphocytes. The samples were stained with hematoxilin and eosine and analyzed at different magnification by a light microscope. Samples obtained from mice injected with LPS alone were compared to samples obtained from mice injected with LPS+recombinant caspase-8. In samples obtained from mice injected with LPS alone, in contrast to those from mice injected also with caspase-8, the paracortex contained multiple dark foci corresponding to dead lymphocytes. Cellular debris was present within the medullary sinuses and was more massive then in caspase 8 treated group. Under higher magnification (×100) of the paracortex region of samples from mice injected with LPS alone, the dark foci were found to be composed of necrotic/apoptotic cellular debris. In mice injected with LPS+caspase-8 the dark foci were smaller and were found much less frequently. Medullary sinuses were found to have clusters of necrotic cellular debris. The necrotic cluster from medullar sinuses of mice injected with LPS or mice injected with LPS+caspase-8 were intracytoplasmic, most probably within a macrophage.

Samples of left and right lymph nodes obtained from 5 mice, each injected at the left and right sides of the back with LPS were stained analyzed as in FIG. 1 and compared (FIG. 2). Multiple dark foci corresponding to dead lymphocytes were detected in all samples. The results summarized in FIG. 2 show that s.c. LPS injections in the right and left sides of the back of the same mouse cause cell death in the paracortex of local inguinal lymph nodes.

Samples of left and right side lymph nodes obtained from 5 mice, each injected at the left and right sides of the back with LPS and co-injected at the right side with caspase-8 were stained, analyzed as in FIG. 1 and compared (FIG. 3). Dark foci were rarely found in samples from lymph node of the right and left side of the animal, i.e. close and far from the caspase-8 injection, respectively. Since the protective effect of caspase-8 was not restricted to the lymph node adjacent to caspase-8 injection, this effect is systemic.

These results show that minute amounts of caspase-8 inhibited accumulation of dead T lymphocytes in inguinal lymph nodes. The results show that s.c. administration of caspase-8 has a systemic effect and as such s.c. administration of caspase-8 can protect the entire organism from massive lymphocyte death.

In contrast to the reported literature on the role of caspase-8 as intracellular inducer or facilitator of apoptosis and on the necessity of blocking caspase-8 in order to alleviate diseases involving massive death of cells, we show herein that injecting caspase-8, attenuates LPS mediated lymphocyte death or accumulation of dead cells in an animal model. These results obtained in vivo, suggest that caspase-8 may act also extracellularly and that the extracellular activity of caspase-8 may be different from the known intracellular activity of the caspase.

Example 2

Figure 4:
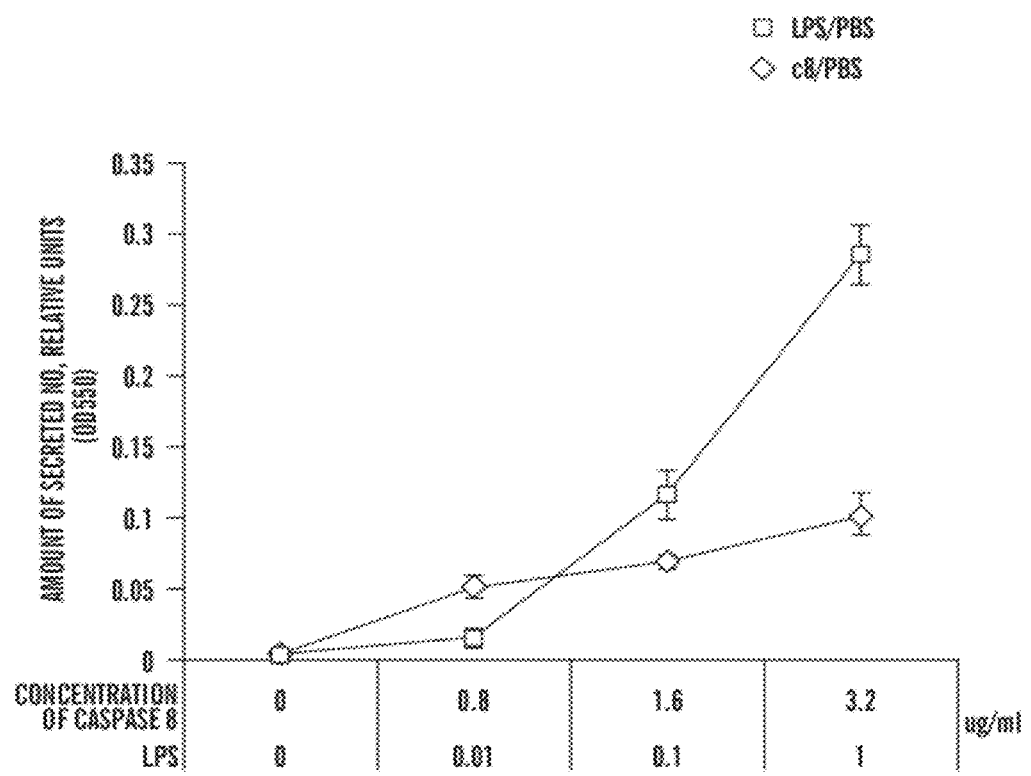
FIG. 4 shows that incubating primary macrophages with recombinant caspase-8 induces a metabolic effect manifested by nitric oxide (NO) secretion by the cells. A culture of peritoneal macrophages was incubated with the indicated concentrations of caspase-8 (c8) or LPS for about 24 hour and the levels of NO secreted to the medium were monitored. The effect of caspase-8 obtained at a concentration 1 µg/ml is comparable with that of LPS at a concentration 0.1 µg/ml.
Figure 5:
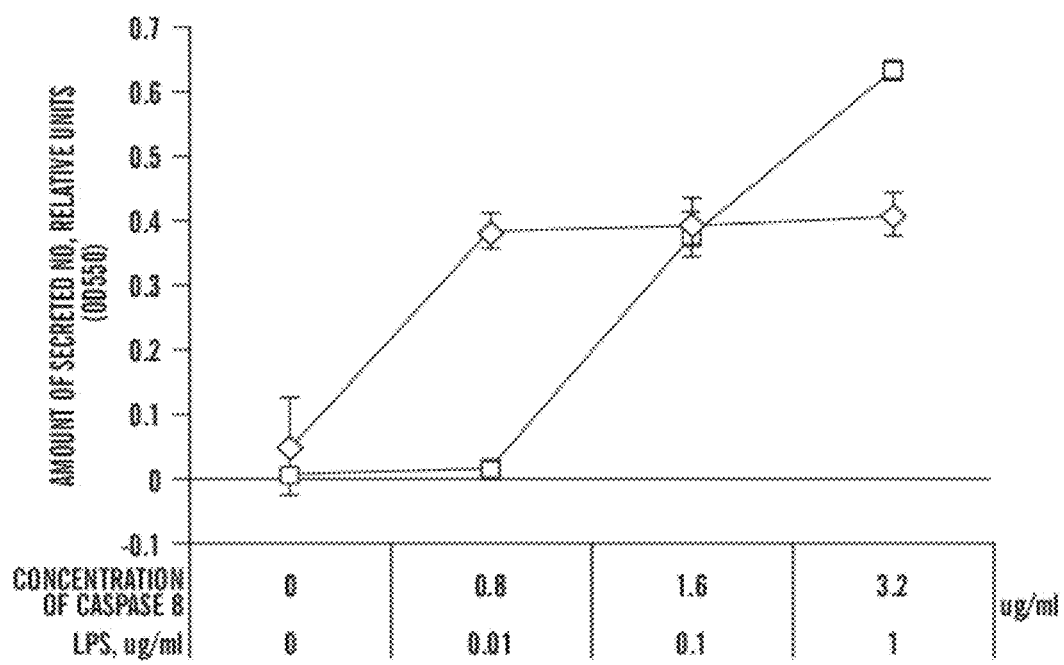
FIG. 5 shows that primary macrophages that were incubated with extracellular caspase-8 continue to secrete NO after caspase-8 withdrawal. The medium of peritoneal macrophages that were incubated for about 24 hours with caspase-8 or LPS as in FIG. 4 was collected and the cells were incubated with fresh medium lacking caspase-8 or LPS for additional 24 hours. Following this period of time, the medium was collected for NO determination.
Figure 6:
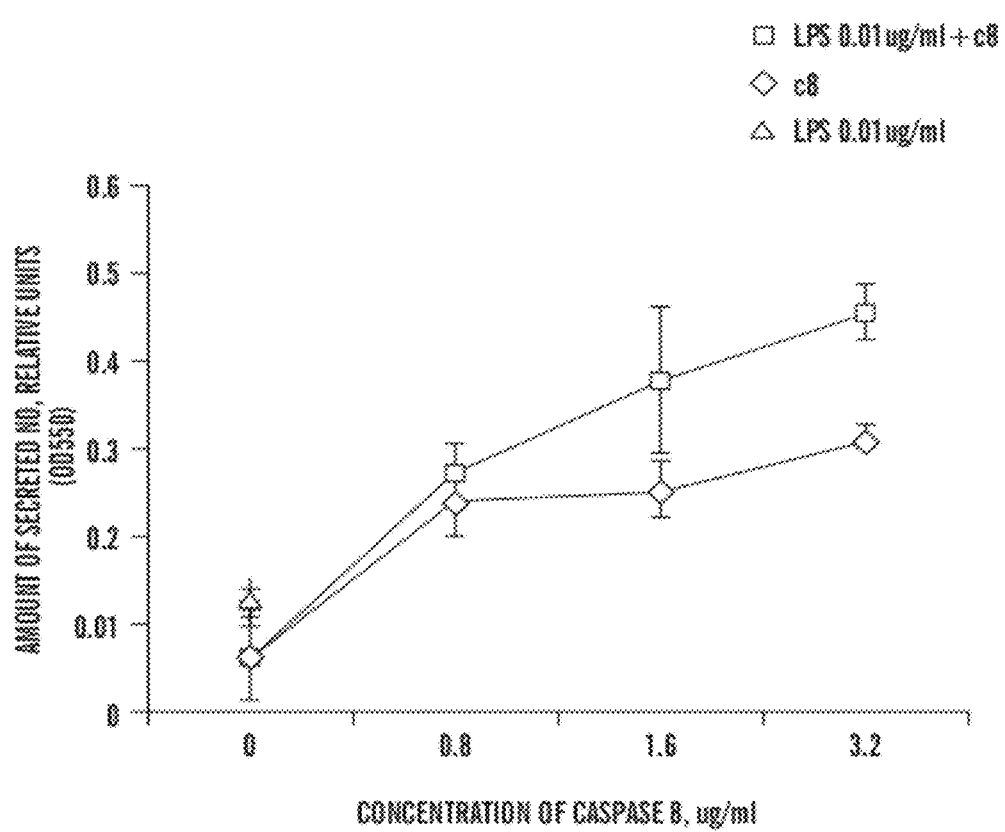
FIG. 6 shows that primary macrophages incubated with caspase-8 secrete NO and that the level of NO secretion is slightly affected by addition of a low dose (0.01 µg/ml) of LPS (a dose unable to stimulate NO secretion by itself).
Figure 7:
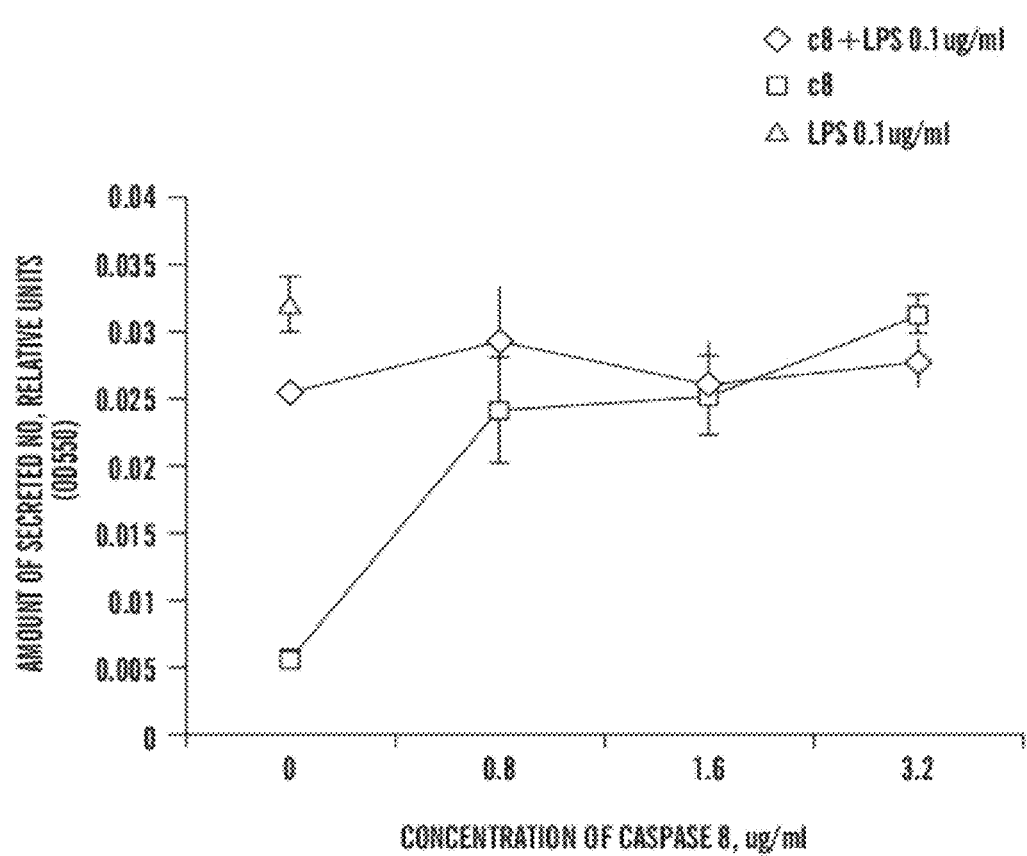
FIG. 7 shows that at a high dose (0.1 µg/ml) of LPS induces NO secretion in primary macrophages and that the level of NO secreted is almost unaffected by addition of caspase-8.

Extracellular Administration of Caspase-8 Induces Nitric oxide (NO) Secretion in a Cell Culture of Peritoneal Macrophages The in vivo results disclosed in example 1 suggest that caspase-8 acts extracellularly. The following experiment was carried out in vitro in order to demonstrate that caspase-8 acts extracellulary and induce metabolic effect on cells. For this purpose, primary macrophages were used. Macrophages activated by LPS are known to produce nitric oxide (NO). Primary macrophages were incubated for about 24 hours with different concentrations of recombinant caspase-8 (0, 0.8, 1.6, and 3.2 µg/ml) or LPS (0, 0.01, 0.1 and 1 µg/ml) and the level of nitric oxide secreted by the cells to the medium was monitored (for details of primary macrophages preparation and/or NO detection, see the material and methods section). We found that incubation of macrophages with recombinant caspase-8 induced NO secretion in such cells in a dose dependent manner (FIG. 4). Remarkably, this effect was observed with caspase-8 in PBS, where it possesses only traces of proteolytic activity. The secretion of NO from macrophages continued after withdrawal of caspase-8 and the levels of NO secreted to the medium mediated by the action of caspase-8 were comparable to the levels of NO secreted to the medium mediated by the action of LPS (FIG. 5). We found that a 48 h incubation of the macrophages after treatment with caspase-8 induced four times higher NO than a 24 h incubation with caspase-8 (FIG. 5 and FIG. 4 3.2 µg/ml caspase-8). The level of NO secreted by macrophages treated with caspase-8 was slightly increased by addition of 0.01 µg/ml LPS (FIG. 6), a dose of LPS which given alone does not stimulate NO secretion (FIG. 4). The effect of 0.1 µg/ml LPS, which induces NO secretion in macrophages (FIG. 4), was not altered by addition of caspase-8 (FIG. 7). The same results were obtained with 1 µg/ml LPS (data not shown).

Figure 8:
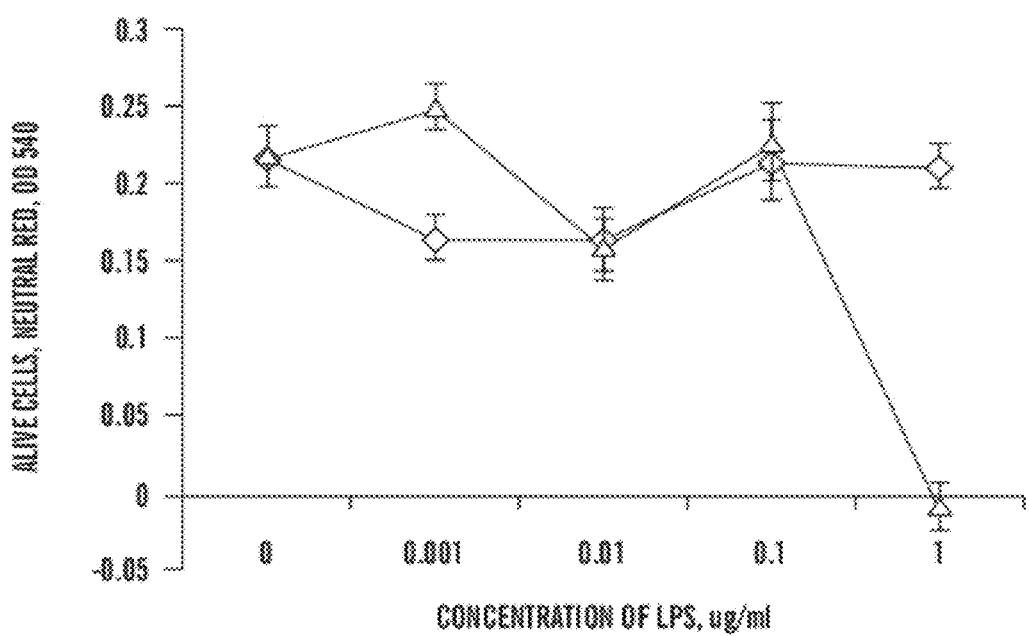
FIG. 8 shows that prolonged incubation of primary macrophages with LPS causes massive cell death. Primary macrophages were incubated with the indicated concentrations of LPS for 19 hours. After this incubation, the cells were maintained in the same medium for additional 27 hours without medium changes or the medium was changed with fresh medium without LPS and the cells were incubated for additional 27 hours. The results obtained show that LPS caused massive cell death, when medium was not changed for 46 hours. Incubation of macrophages with LPS and without medium change is indicated with filled triangles.
Figure 9:
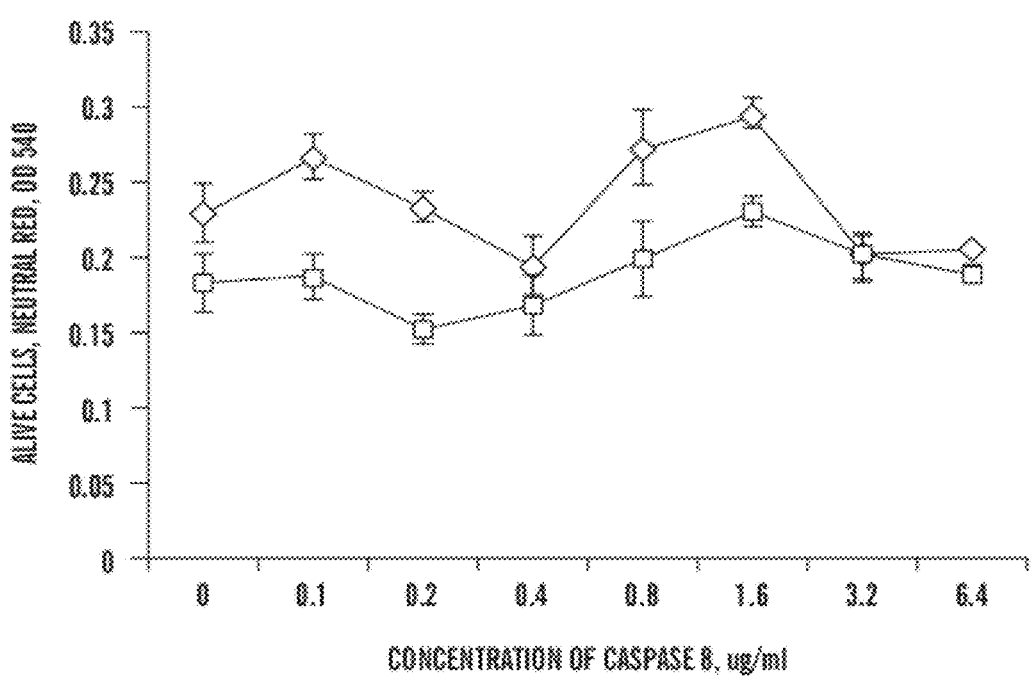
FIG. 9 shows that prolonged incubation of primary macrophages with caspase-8 does not affect survival of the cells. Primary macrophages were incubated with the indicated concentrations of caspase-8 for 18 hours. After this incubation, the cells were maintained in the same medium for additional 29 hours without medium changes or the medium was changed with fresh medium without caspase-8 and the cells were incubated for additional 29 hours. The results show that caspase-8 was not cytotoxic to the macrophages when medium was not changed for 47 h. Incubation of macrophages with caspase-8 and without medium change is indicated with filled squares.

The following experiment was designed to find out whether prolonged exposure of macrophages to caspase-8 is cytotoxic. Primary macrophages were incubated with different concentrations of LPS or caspase-8 for 46/47 hours, with or without one change of medium lacking LPS and caspase-8 after 16/17 hours, and survival of the cells was determined. Incubation of macrophages with 1 µg/ml LPS for 46 h, without change of medium, induced massive death of the macrophages (FIG. 8). In contrast, none of the caspase-8 concentrations employed for 47 hours in the absence of medium changes were cytotoxic for macrophages (FIG. 9).

The results obtained show that extra-cellular application of caspase-8 affects functions of macrophage cells, and that extra-cellular caspase-8, unlike intracellular caspase-8, does not cause the death of cells.

References

Ashina M. Nitric oxide synthase inhibitors for the treatment of chronic tension-type headache. Expert Opin Pharmacother. 2002 April; 3(4):395-9. Review.

Ballester I, Gonzalez R, Nieto A, Zarzuelo A, de Medina F S. Monochloramine induces acute and protracted colitis in the rat: response to pharmacological treatment. Life Sci. May 6; 76(25):2965-80. 2005

Bommhardt et al. (2004) Bommhardt U, Chang K C, Swanson P E, Wagner T H, Tinsley K W, Karl I E, Hotchkiss R S. Akt decreases lymphocyte apoptosis and improves survival in sepsis. J. Immunol. Jun. 15; 172(12):7583-91. 2004

Bradford Sanders D, Hunter K, Wu Y, Jablonowski C, Bahl J J, Larson D F. Related Articles, Links Modulation of the inflammatory response in the cardiomyocyte and macrophage. J Extra Corpor Technol. September; 33(3): 167-74. 2001

Castro A, Bemer V, Nobrega A, Coutinho A, Truffa-Bachi P. Administration to mouse of endotoxin from gram-negative bacteria leads to activation and apoptosis of T lymphocytes. Eur J. Immunol. February; 28(2):488-95. 1998.

Chen T, Zamora R, Zuckerbraun B, Billiar T R. Role of nitric oxide in liver injury. Curr Mol. Med. 2003 September; 3(6):519-26. Review.

Childress B B, Stechmiller J K. Role of nitric oxide in wound healing. Biol Res Nurs. 2002 July; 4(1):5-15. Review.

Ebadi M, Sharma S K Peroxynitrite and mitochondrial dysfunction in the pathogenesis of Parkinson's disease. Antioxid Redox Signal. 2003 June; 5(3):319-35. Review.

Fleming S D, Campbell P A. Macrophages have cell surface IL10 that regulates macrophage bactericidal activity. J. Immunol, v. 156: 1143-1150. 1996.

Garthwaite J. Glutamate, nitric oxide and cell-cell signalling in the nervous system. Trends Neurosci. 1991 February; 14(2):60-7. Review.

Harter L, Keel M, Hentze H, Leist M, Ertel W. Caspase-3 activity is present in cerebrospinal fluid from patients with traumatic brain injury. J. Neuroimmunol. Dec. 3; 121(1-2): 76-8. 2001

Hentze H, Schwoebel F, Lund S, Keel M, Ertel W, Wendel A, Jaattela M, Leist M. In vivo and in vitro evidence for extracellular caspase activity released from apoptotic cells. Biochem Biophys Res Commun. 2001 May 25; 283(5): 1111-7. Erratum in: Biochem Biophys Res Commun Jul. 27; 285 (4):1076. 2001

Mattana J, Margiloff L, Chaplia L, Chow A, Singhal P C. Metal-catalyzed oxidation of extracellular matrix increases macrophage nitric oxide generation. Kidney Int. November; 54(5):1581-92. 1998

Matsushita K, Morrell C N, Cambien B, Yang S X, Yamakuchi M, Bao C, Hara M R, Quick R A, Cao W, O'Rourke B, Lowenstein J M, Pevsner J, Wagner D D, Lowenstein C J. Nitric oxide regulates exocytosis by S-nitrosylation of N-ethylmaleimide-sensitive factor. Cell. 2003 Oct. 17; 115(2):139-50.

Nathan C F, Hibbs J B Jr. Related Role of nitric oxide synthesis in macrophage antimicrobial activity. Curr Opin Immunol. 1991 February; 3(1):65-70. Review.

Neufeld A H. Pharmacologic neuroprotection with an inhibitor of nitric oxide synthase for the treatment of glaucoma. Brain Res Bull. Feb. 15; 62(6):455-9. 2004.

Palmer R M, Ferrige A G, Moncada S, Nitric oxide release accounts for the biological activity of endothelium-derived relaxing factor. Nature. 1987 Jun. 11-17; 327(6122):524-6.

Park J E, Barbul A. Understanding the role of immune regulation in wound healing. Am J. Surg. 2004 May; 187 (5A):11S-16S. Review.

Rekka E A, Chrysselis M C. Nitric Oxide and atherosclerosis. Mini Rev Med Chem, 2002, 6: 585-93

Salerno L, Sorrenti V, Di Giacomo C, Romeo G, Siracusa M A. Progress in the development of selective nitric oxide synthase (NOS) inhibitors. Curr Pharm Des. 2002; 8(3): 177-200. Review.

Shavali S, Combs C K, Ebadi M. Reactive macrophages increase oxidative stress and alpha-synuclein nitration during death of dopaminergic neuronal cells in co-culture: relevance to Parkinson's disease. Neurochem Res. January; 31(1):85-94. 2006

Sun Q, Wang A, Jin X, Natanzon A, Duquaine D, Brook R D, Aguinaldo J G, Fayad Z A, Fuster V, Lippmann M, Chen L C, Rajagopalan S. Long-term air pollution exposure and acceleration of atherosclerosis and vascular inflammation in an animal model. JAMA. Dec. 21; 294(23):3003-10. 2005

Toda N, Ayajiki K, Okamura T. Nitric oxide and penile erectile function. Pharmacol Ther. 2005 May; 106(2):233-66. Epub 2005 Mar. 2. Review.

Wesche D E, Lomas-Neira J L, Perl M, Chung C S, Ayala A. Leukocyte apoptosis and its significance in sepsis and shock. J Leukoc Biol. August; 78(2):325-37. 2005.

Wesche-Soldato D E, Chung C S, Lomas-Neira J, Doughty L A, Gregory S H, Ayala A. In vivo delivery of caspase-8 or Fas siRNA improves the survival of septic mice. Blood. Oct. 1; 106(7):2295-301. 2005

Willmot M, Gibson C, Gray L, Murphy S, Bath P. Nitric oxide synthase inhibitors in experimental ischemic stroke and their effects on infarct size and cerebral blood flow: a systematic review. Free Radic Biol Med. 2005 Aug. 1; 39(3):412-25. Epub 2005 Apr. 12.

The invention claimed is:

1. A method for increasing nitric oxide (NO) production in an individual having an inflammatory condition, the method comprising administering to the individual a therapeutically effective amount of caspase-8, a mutein comprising an amino acid sequence at least 90% identical to that of caspase-8, or a functional derivative or salt of caspase-8, wherein said functional derivative is derived by one or more derivatizations selected independently from the group consisting of attachment of polyethylene glycol to an amino acid side chain, esterification with an aliphatic ester or a carboxyl group, amidation of a carboxyl group, N-acyl derivatization of an amino group, and O-acyl derivatization of a hydroxyl group and a pharmaceutically acceptable carrier.

2. The method of claim 1, wherein the individual having an inflammatory condition has pain of angina.

3. A method of treating sepsis, the method comprising administering to the individual having sepsis a therapeutically effective amount of caspase-8, a mutein comprising an amino acid sequence at least 90% identical to that of caspase-8, or a functional derivative or salt of caspase-8, wherein said functional derivative is derived by one or more derivatizations selected independently from the group consisting of attachment of polyethylene glycol to an amino acid side chain, esterification with an aliphatic ester or a carboxyl group, amidation of a carboxyl group, N-acyl derivatization of an amino group, and O-acyl derivatization of a hydroxyl group and a pharmaceutically acceptable carrier.

4. A method of treating erectile dysfunction the method comprising administering to the individual having erectile dysfunction a therapeutically effective amount of caspase-8, a mutein comprising an amino acid sequence at least 90% identical to that of caspase-8, or a functional derivative or salt of caspase-8, wherein said functional derivative is derived by one or more derivatizations selected independently from the group consisting of attachment of polyethylene glycol to an amino acid side chain, esterification with an aliphatic ester or a carboxyl group, amidation of a carboxyl group, N-acyl derivatization of an amino group, and O-acyl derivatization of a hydroxyl group and a pharmaceutically acceptable carrier.

* * * * *